(12) United States Patent
Paul, Jr. et al.

(10) Patent No.: US 8,540,760 B2
(45) Date of Patent: Sep. 24, 2013

(54) TUBULAR DEVICES HAVING REVERSIBLE COMPONENTS FOR DEPLOYMENT OF ENDOLUMINAL OCCLUDERS AND RELATED METHODS AND SYSTEMS

(75) Inventors: Ram H. Paul, Jr., Bloomington, IN (US); Jacob A. Flagle, Bloomington, IN (US); Brian C. Case, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1182 days.

(21) Appl. No.: 12/164,520

(22) Filed: Jun. 30, 2008

(65) Prior Publication Data

US 2009/0018637 A1 Jan. 15, 2009

Related U.S. Application Data

(60) Provisional application No. 60/949,057, filed on Jul. 11, 2007.

(51) Int. Cl.
*A61F 2/84* (2006.01)
(52) U.S. Cl.
USPC .......................................... 623/1.12; 606/200
(58) Field of Classification Search
USPC ............... 623/1.11, 1.12, 1.2, 1.49; 606/200, 606/191, 194, 195, 198
See application file for complete search history.

(56) References Cited

U.S. PATENT DOCUMENTS

| | | | |
|---|---|---|---|
| 3,506,011 A | 4/1970 | Silverman | |
| 3,911,927 A | 10/1975 | Rich et al. | |
| RE31,855 E | 3/1985 | Osborne | |
| 4,604,094 A | 8/1986 | Shook | |
| 4,732,152 A | 3/1988 | Wallsten et al. | |
| 4,848,343 A | 7/1989 | Wallsten et al. | |
| 5,993,427 A | 11/1999 | Rolland et al. | |
| 6,004,328 A | 12/1999 | Solar | |
| 7,632,296 B2 * | 12/2009 | Malewicz | 623/1.11 |
| 7,857,825 B2 * | 12/2010 | Moran et al. | 606/200 |
| 2003/0212373 A1 | 11/2003 | Hall et al. | |
| 2004/0097957 A1 | 5/2004 | Jaker et al. | |
| 2005/0283182 A1 * | 12/2005 | Pierce et al. | 606/200 |
| 2008/0281398 A1 * | 11/2008 | Koss et al. | 623/1.12 |

FOREIGN PATENT DOCUMENTS

| | | |
|---|---|---|
| EP | 0668086 | 8/1995 |
| WO | WO 2006119256 | 11/2006 |

OTHER PUBLICATIONS

PCT/US08/069290 International Search Report, 5 pages.
PCT/US08/069290 Written Opinion, 9 pages.
PCT/US08/069290 International Search Report, 5 pages, Date: Sep. 23, 2008.

* cited by examiner

*Primary Examiner* — Vy Q Bui
(74) *Attorney, Agent, or Firm* — Woodard, Emhardt, Moriarty, McNett & Henry LLP

(57) ABSTRACT

Described are devices, methods, and systems useful for deploying one or more occlusive prostheses within the vasculature of a patient. Illustrative devices can include a deployment tube or sheath that contains an occlusive prosthesis, wherein a segment of the sheath is reversible by a user so as to deploy the prosthesis from the sheath lumen within a bodily lumen of a patient.

24 Claims, 13 Drawing Sheets

TUBULAR DEVICES HAVING REVERSIBLE COMPONENTS FOR DEPLOYMENT OF ENDOLUMINAL OCCLUDERS AND RELATED METHODS AND SYSTEMS

REFERENCE TO RELATED APPLICATIONS

The present application claims the benefit of U.S. Provisional Patent Application Ser. No. 60/949,057 filed Jul. 11, 2007, entitled TUBULAR DEVICES HAVING REVERSIBLE COMPONENTS FOR DEPLOYMENT OF ENDOLUMINAL OCCLUDERS AND RELATED METHODS AND SYSTEMS which is hereby incorporated by reference in its entirety.

BACKGROUND

The present invention resides generally in the field of devices and methods useful for the occlusion of vascular vessels, and in a particular aspect relates to the occlusion of the greater saphenous vein to treat complications, such as varicose vein condition, resultant of venous reflux.

As further background, vascular vessels are comprised of tissue and are the conduit for circulating blood through a mammalian body. A vascular vessel that carries blood from the heart is known as an artery. A vascular vessel that returns blood to the heart is known as a vein. There are three types of veins in a human: deep veins, which are located deep in the body close to the bones, superficial veins, which are located close to the skin, and perforating veins, which are smaller veins that connect the deep veins to the superficial veins.

To assist blood flow, venous vascular vessels contain venous valves. Each venous valve is located inside the vein and typically includes at least two valve leaflets, which are disposed annularly along the inside wall of the vein. These leaflets open to permit blood flow toward the heart and close, upon a change in pressure, such as a transition from systole to diastole, to restrict the back flow of blood. When blood flows towards the heart, the venous pressure forces the valve leaflets to move apart in a downstream flexing motion, thereby creating an open path for blood flow. The leaflets normally flex together when moving in the upstream direction; therefore, they return to a closed position to restrict or prevent blood flow in the upstream, or retrograde, direction after the venous pressure is relieved. The leaflets, when functioning properly, extend radially inward toward one another such that the leaflet tips, or cusps contact each other when the valve is closed.

On occasion, and for a variety of reasons, such as congenital valve or vein weakness, disease in the vein, obesity, pregnancy, and/or an occupation requiring long periods of standing, one or more valves in a vein will allow deleterious retrograde flow to occur. When a valve allows such retrograde flow, blood will collect, or pool in vessels beneath the valve. This pooling of blood causes an increase in the venous pressure below the valve. Venous valves that allow such deleterious retrograde flow are known as incompetent or inadequate venous valves. The condition resulting from such incompetent venous valves is known as venous valve insufficiency.

In the condition of venous valve insufficiency, the venous valve leaflets do not function properly. Incompetent venous valves can cause the veins to bulge, can cause swelling in the patient's lower extremities, and can result in varicose veins and/or chronic venous insufficiency. If left untreated, venous valve insufficiency can cause venous stasis ulcers of the skin and subcutaneous tissue.

A common method of treatment for venous valve insufficiency is the placement of an elastic stocking around the patient's leg to apply external pressure to the vein, forcing the walls radially inward to force the leaflets into apposition. Although sometimes successful, the tight stocking is quite uncomfortable, especially in warm weather, because the stocking must be constantly worn to keep the leaflets in apposition. The elastic stocking also affects the patient's physical appearance, thereby potentially having an adverse psychological affect. This physical and/or psychological discomfort can lead to the patient removing the stocking, thereby inhibiting treatment.

Surgical methods for treatment of venous valve insufficiency have also been developed. A vein with incompetent venous valves can be surgically constricted to bring incompetent leaflets into closer proximity in hopes of restoring natural valve function. Methods for surgical constriction of an incompetent vein include implanting a frame around the outside of the vessel, placing a constricting suture around the vessel (e.g., valvuloplasty), or other types of treatment to the outside of the vessel to induce vessel contraction. Other surgical venous valve insufficiency treatment methods include bypassing or replacing damaged venous valves with autologous sections of veins containing competent valves.

Another surgical method includes vein stripping and ligation. In this procedure, the femoral vein and other major venous tributaries are disconnected from the greater saphenous vein (GSV) and tied off. Next, the GSV is removed from the leg by advancing a wire through the vein, tying the wire to a saphenous vein end, and then pulling the wire, and vein, out through an incision in the upper calf or ankle. Unfortunately, the above surgeries require at least one incision and have several undesirable side effects and risks, such as a long patient recovery time, the potential for scarring, and numerous other risks inherent with surgery, such as those associated with the administration of anesthesia.

Recently, various implantable prosthetic devices and minimally invasive methods for implantation of these devices have been suggested to treat venous valve insufficiency. Such prosthetic devices can be inserted intravascularly, for example from an implantation catheter. Prosthetic devices can function as a replacement venous valve, or enhance venous valve function by bringing incompetent valve leaflets into closer proximity. In one procedure, venous valve function can be enhanced by clipping the valve leaflets together with a clip made from a biocompatible material, such as a metal or polymer. In other procedures, valve leaflets can be attached using a plastic or metal staple or can be fastened with sutures.

Recently, a number of methods have been suggested to treat varicose veins and venous valve leaflets with energy sources, such as radiofrequency (RF) energy. In one such method, valve leaflets can be fastened together with electrodes delivering RF energy. In another such method, a catheter having an electrode tip can be used to apply RF energy to cause localized heating and corresponding shrinkage of venous tissue. After treatment of one venous section is complete, the catheter can be repositioned to treat a different venous section.

Methods for treatment of varicose veins have also been developed involving various forms of sclerotherapy. Generally, sclerotherapy involves the delivery of one or more sclerosing agents to the lumen of a vein, which induce the vein to collapse and the venous walls to fuse, thereby occluding the vein.

In view of this background, the need remains for improved and alternative techniques, devices and systems for affecting the venous system to treat venous conditions. The present invention is addressed to these needs.

SUMMARY OF THE INVENTION

Accordingly, in one aspect, the present invention provides a medical device for deploying one or more occlusive prostheses within a patient that includes a tube or sheath that has a reversible component. In certain aspects, the reversible component can contain an occlusion device and can be reversed by a user to deploy the occlusion device within a lumen of a patient.

In another aspect, the present invention provides a medical product for the delivery of a prosthesis within the vasculature of a patient that includes a sponge form prosthesis contained within a reversible segment of a cannulated device, wherein the reversible segment is reversible by a user so as to deploy the sponge form prosthesis within the vasculature of the patient. In certain aspects, the reversible segment includes a sleeve that is slidably received within the cannulated lumen.

In yet another aspect, the present invention provides an endoluminal medical product that includes a percutaneous deployment sheath having a proximal end, a distal end, and a lumen. A sleeve having a proximal end, a distal end, and a lumen is slidably received within the lumen of the sheath and the distal end of the sleeve extends from and reverses over the distal end of the sheath. The sleeve is configured to deploy one or more remodelable prostheses from a constrained position within the sleeve lumen to an expanded position within a patient's vasculature by reversing the sleeve around the distal end of the sheath.

In still yet another aspect, the present invention provides a medical product for the deployment of one or more prostheses within a bodily lumen of a patient that includes a cannulated device having a proximal end, a distal end, and a wall that defines a lumen and occupies an invertible segment. The invertible wall segment is located at the distal end of the cannulated device and the invertible segment is inverted within the lumen of the cannulated device and contains one or more bioremodelable prostheses. The invertible wall segment is evertable by a user from its inverted position within the device lumen so as to deploy the one or more prostheses within a bodily lumen of a patient.

In yet another aspect, the present invention provides a method for treating a vascular deficiency that includes providing a cannulated device having a proximal end, a distal end, and a lumen that defines a wall. The distal end of the wall is inverted within the lumen of the cannulated device and the inverted wall segment contains one or more remodelable prostheses. The inverted wall segment is evertable by a user to expose the contents of the cannulated lumen and to deliver the one or more remodelable prostheses into a vascular vessel. The method continues by locating the distal end of the provided device at a vascular site within the vascular vessel, and thereafter deploying the one or more prostheses at the vascular site by everting the inverted wall segment so as to deliver the prostheses within the vascular vessel at the vascular site.

In still yet another aspect, the present invention provides a method for treating a refluxing saphenous vein that includes providing a cannulated device having a proximal end, a distal end, a wall that defines a lumen, and a segment or portion that is reversible by a user. The reversible portion contains an occlusive prosthesis and the reversible portion is evertable to deploy the occlusive prosthesis within a saphenous vein of a patient. The method continues by locating the provided cannulated device within the saphenous vein, and thereafter delivering the occlusive prosthesis within the vein by everting the reversible portion of the cannulated device to deploy the prosthesis within the vein.

In still yet another aspect, the present invention provides a medical product that includes a cannulated device having a wall that defines a lumen. The wall occupies a first wall region and a second reversible wall region. The second wall region has a wall diameter that, when not inverted, decreases in a distal direction along the length of the second wall region. Additionally, the wall of the second wall region is inverted within the lumen of the first wall region and the inverted wall portion contains one or more prostheses. The inverted wall portion is evertable by a user to deploy the one or more prostheses within a bodily lumen of a patient.

In yet another aspect, the present invention provides a method for loading a delivery device with one or more prostheses that includes providing a cannulated device having a proximal end, a distal end, and a wall that defines a lumen. A segment or portion of the device is reversible by a user and the reversible segment of the device is in a reversed position. The method continues by placing one or more prostheses adjacent the reversed portion of the provided device and thereafter enclosing the one or more placed prostheses within the lumen of the cannulated device. In certain aspects, the reversed segment of the device is an inverted segment of the cannulated device wall.

In yet another aspect, the present invention includes a medical kit that includes a medical product of the invention enclosed in sterile medical packaging. In certain aspects, the medical product includes a device for the delivery of a prosthesis within the vasculature of a patient that includes a sponge form prosthesis contained within a reversible segment of a cannulated device, wherein the reversible segment is reversible by a user so as to deploy the sponge form prosthesis within the vasculature of the patient. In certain aspects, the reversible segment includes a sleeve that is slidably received within the cannulated lumen.

The present invention provides improved and/or alternative methods, systems, and devices for deploying occlusive prostheses within the vasculature or other bodily vessels of a patient. Additional embodiments as well as features and advantages of the invention will be apparent from the further descriptions herein.

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the present invention provide methods, devices, and systems for deploying occlusive devices within vascular vessels in the treatment of certain vascular deficiencies, such as those involved in venous valve insufficiency (VVI). For example, a cannulated deployment device containing one or more prostheses within a reversible segment of the device can be located within a venous vessel and the one or more prostheses can be deployed within the vessel by reversing or actuating the reversible segment of the device. In certain aspects, the reversible device segment can include a reversible sleeve that is slidably received within the cannulated device and that is actuatable around the distal device end to deploy one or more occlusion devices within the venous system to treat certain varicosities resulting from VVI. Advantageous such deployable occlusive devices can include devices that exhibit a low radial force and/or devices that tend to buckle, compress, or twist under frictional forces that can be caused by deployment and/or loading techniques that involve the movement of the prosthesis against a stationary wall.

Figure 1:
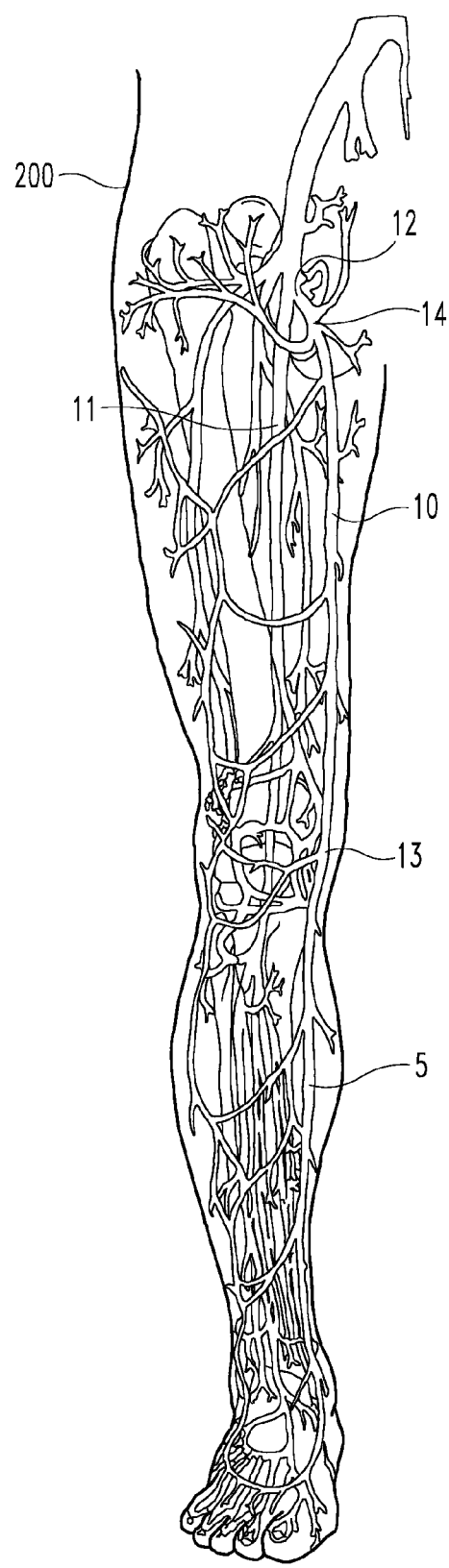
FIG. 1 depicts a human leg showing certain venous structures therein.
Figure 2:
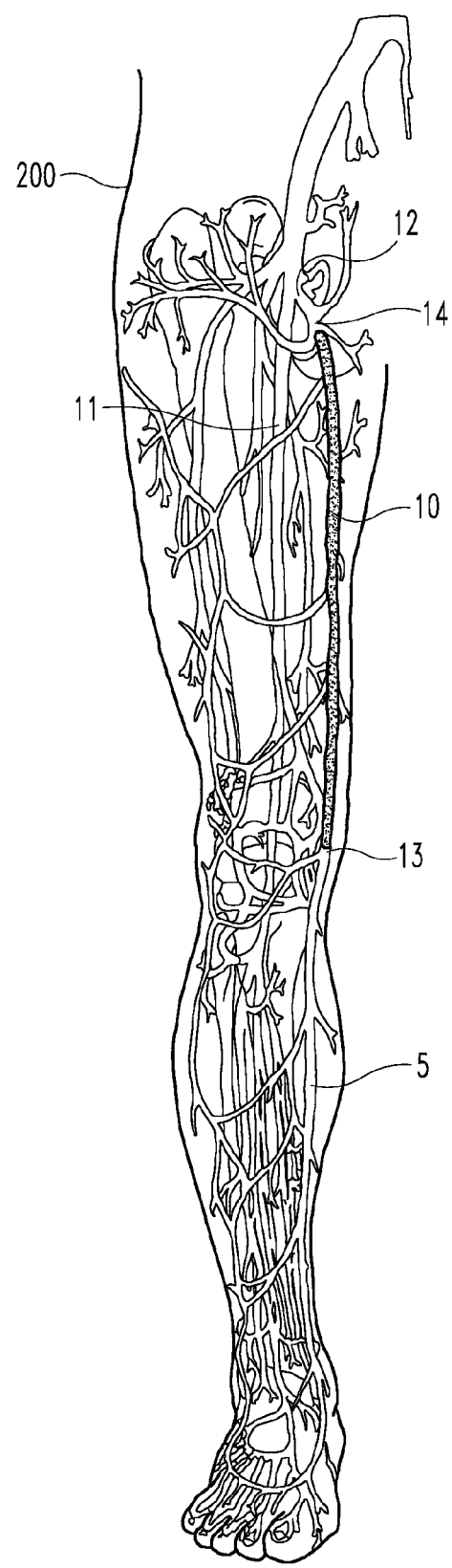
FIG. 2 depicts a human leg showing certain venous structures therein.

With reference now more particularly to the figures, shown in FIG. 1 is a diagram of a human leg showing certain venous structures therein. In particular, shown is human leg 200 having greater saphenous vein (GSV) 10 and femoral vein 11 which adjoin at the sapheno-femoral junction 12. In accordance with certain aspects of the present invention, the GSV 10 can be occluded in a region constituting substantially all of the passage between a point 13 occurring near the medial side of the knee to a point 14 occurring prior to the sapheno-femoral junction 12, as illustrated by the shaded area in FIG. 2. Desirably, such occlusion is effective to prevent the undesirable reflux of venous blood from the sapheno-femoral junction 12 in a direction down toward the medial side of the knee (e.g. at point 13). Such occlusion is effective to treat varicosities that commonly occur in lower portions of the leg, e.g. portions occurring below the knee.

Figure 3:
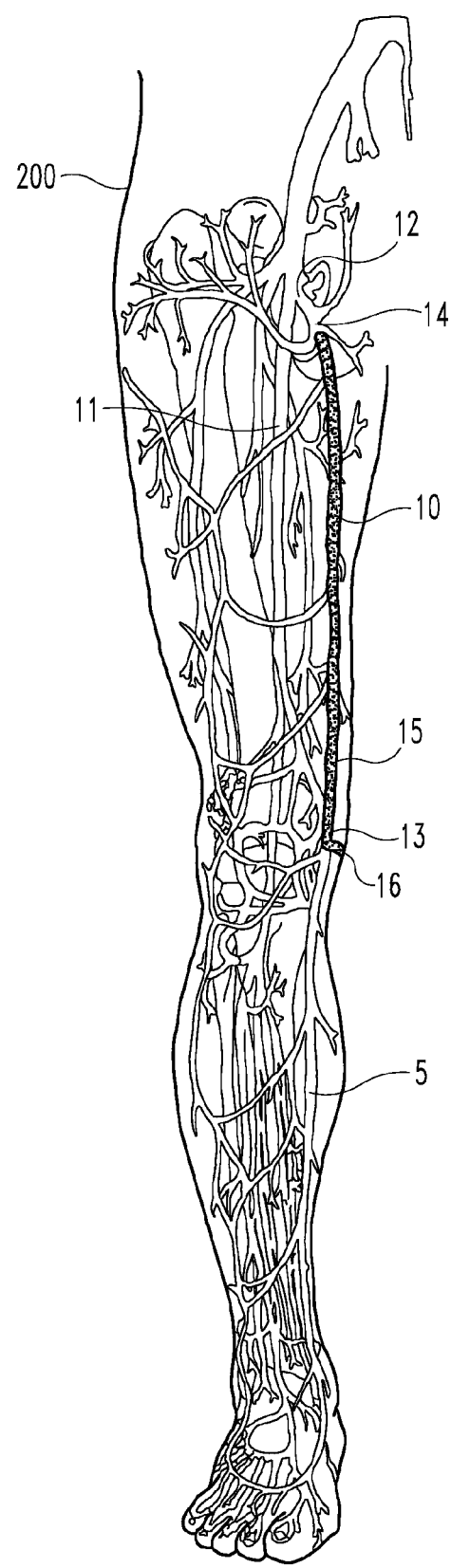
FIG. 3 depicts a human leg showing certain venous structures therein.

More specifically now, with reference to FIG. 3, in certain forms of the invention, occlusion of the passage of the GSV occurring between points 13 and 14 can be achieved by an occlusion device 15 that extends from point 13 to point 14, and that may include an end portion 16 that traverses the wall of the GSV 10. This may be achieved by deploying an occlusion device 15 during a percutaneous procedure, e.g. as described herein. Illustratively, the occlusion device can comprise a remodelable sheet material, in folded form for example, or a remodelable sponge form material that is highly expansible upon wetting, as are discussed in further detail herein.

Turning now to a brief overview of illustrative deployment devices and procedures of the invention, with general reference to FIGS. 4 through 7D, in certain aspects, a device, such as a cannulated device, e.g. a sheath or tube, can have a reversible component or segment that is configured to deploy one or more occlusive or other devices within a patient's vasculature. For example, in certain embodiments, a deployment device can include a reversible sleeve that is slidably disposed within the lumen of a sheath. An occlusion device can be loaded within the reversible sleeve component and can be deployed within a venous vessel by reversing the reversible sleeve over an end of the sheath. In alternative embodiments, a deployment device can include a sheath having a distal end or tip that includes a reversible or foldable wall segment. An occlusive device can be loaded within the sheath lumen by inverting the reversible wall segment of the sheath such that the reversible wall segment overlays or contains the occlusive device at a location within the lumen of the sheath. The occlusive device can thereafter be deployed within a bodily vessel by everting a portion of the reversible wall segment from its inverted position within the sheath lumen. In still alternative embodiments, a deployment device can include a sheath having an evertable wall section that contains or houses an occlusive prosthesis that can be deployed within the vasculature of a patient by reversing or outwardly folding at least a portion of the evertable wall segment.

Figure 4A:
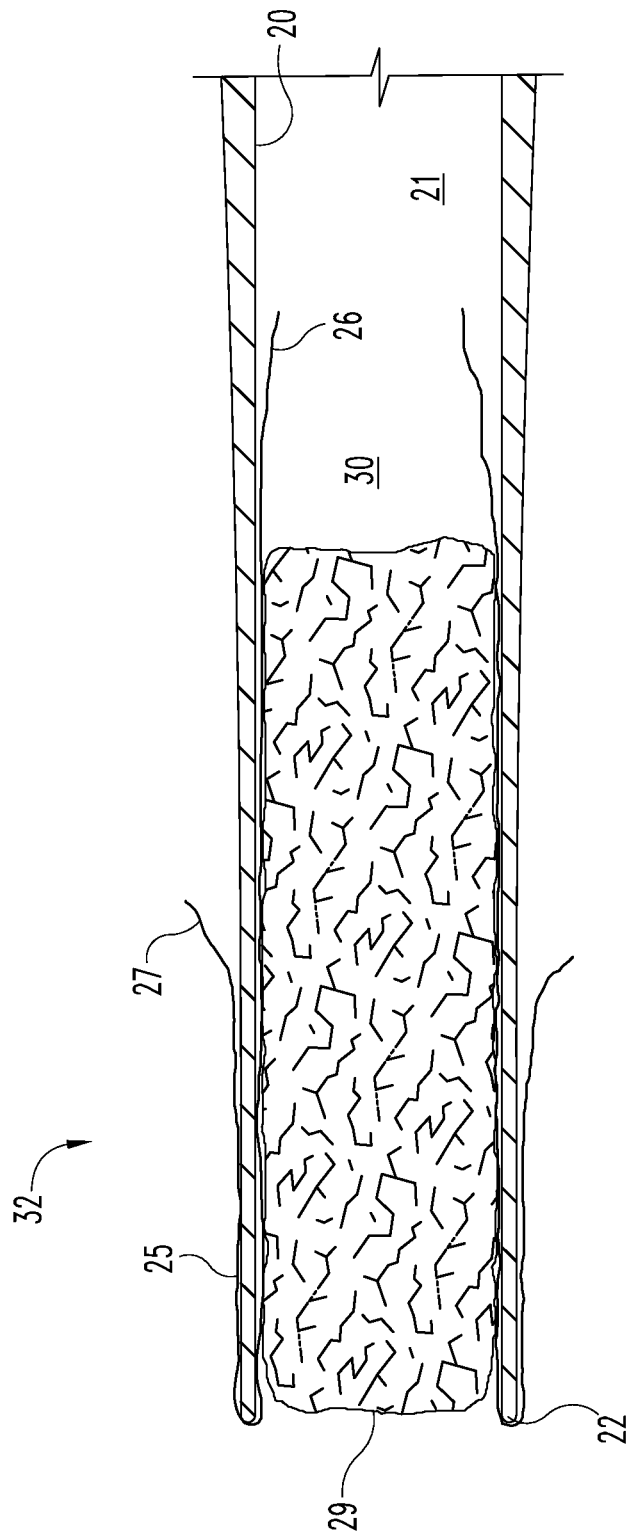
FIG. 4A depicts a cross-sectional view of an illustrative deployment device that can be useful in certain embodiments of the invention.

Turning now to a more detailed discussion of illustrative deployment devices of the invention, with reference to the cross-sectional view of FIG. 4A, a medical product 32 is depicted that can comprise a cannulated device 20 that has a relatively constant inner diameter and an outer diameter that gradually tapers downward from the proximal device end (not shown) toward the cannulated device's 20 distal end 22. A tubular sleeve 25 having open proximal 26 and distal 27 ends can be slidably received within the lumen 21 of the sheath 20, such that the distal end 27 of the sleeve 25 reverses around the distal end 22 of the sheath 20 and extends along the wall of the sheath in a proximal direction. Additionally, a sponge form occlusion device 29 can be contained within the lumen 30 of the sleeve 25. The distal end of the occlusion device 29 can be positioned relative to the distal end 22 of the sheath 20 by slidably moving the sleeve 25 within the lumen of the sheath 20. For example, in certain embodiments, the occlusion device 29 can be positioned within the sheath 20 such that the distal end of the device 29 is located inside the sheath lumen 21, or, in alternative embodiments, the occlusion device 29 can be positioned such that its distal end extends from the sheath lumen to form an atraumatic tip at the distal end of the medical device 32, for example.

Figure 4B:
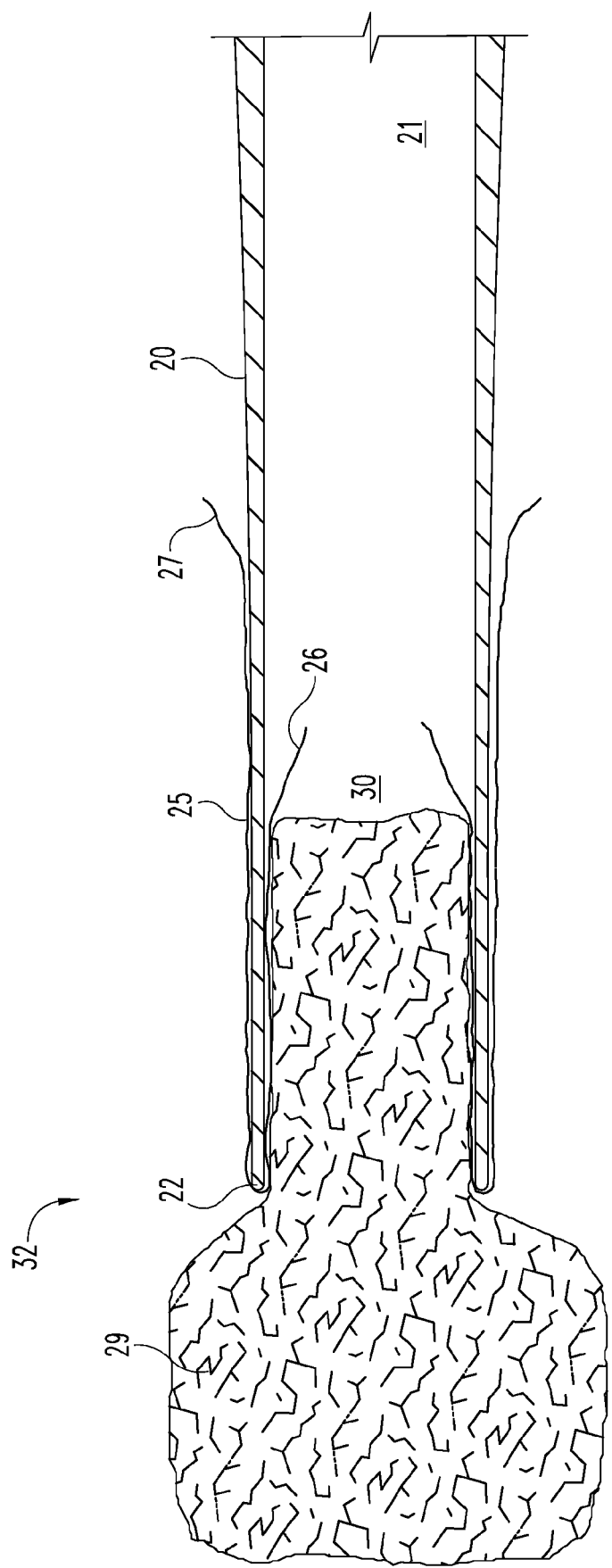
FIG. 4B depicts a cross-sectional view of an illustrative deployment device that can be useful in certain embodiments of the invention.

Turning now to the cross-sectional view of FIG. 4B, in certain embodiments, the medical product 32 can be positioned within a suitable bodily lumen (not shown) and the occlusion device 29 can be deployed by reversing the sleeve 25 around the distal end 22 of the cannulated device 20. Illustratively, the distal end 27 of the reversed sleeve 25 can be actuatable from an extracutaneous position to deploy the prosthesis 29. For example, the sleeve 25 can be of sufficient length such that the distal end 27 of the reversed sleeve 25 extends to an extracutaneous location when the distal end 22 of the sheath 20 is located at the deployment site. In alternative embodiments, however, the distal end 27 of the sleeve 25 can be actuated from an intracutaneous location, e.g. within a bodily vessel, by attaching one or more leaders to the distal end 27 of the sleeve, wherein such leaders can extend to an extracutaneous location where they can be actuated to reverse the sleeve 25 and deploy the prosthesis 29. Illustrative such actuators can include one or more control wires, in mesh form around the sheath if desirable, or plastic strips or bands that extend longitudinally along the sheath 20 wall. Additionally, the one or more leaders, along with the reversed portion of the sleeve 25, can be received within a sheath or tube (not shown) that can be slidably received over the deployment sheath 20 in an annular fashion. Optionally, the annularly received sheath can be connected to the deployment sheath 20 in order to fix its position in relation to the deployment sheath 20, if desirable.

With reference still to FIG. 4B, in certain deployment embodiments, the occlusion device 29 can be deployed in a distal direction from the sheath lumen 21 by reversing the sleeve 25 while maintaining the sheath's 20 position at a substantially constant location within the patient. In alternative embodiments, however, the occluder 29 can be deployed in a substantially steadfast location within the patient by reversing the sleeve 25 while moving the sheath 20 in a proximal direction. Additionally, deployment of the occlusion device 29 can be facilitated by locating a push rod or pusher (not shown) within the lumen 21 of the sheath 20 and thereafter advancing the pusher against the proximal end of the occluder 29 while simultaneously reversing the sleeve 25 over the sheath. Still additionally, the sleeve 25 can be modified to assist with device 29 deployment or otherwise, by closing the proximal end 26 of the sleeve to form a sock, for example, which can then be attached to the proximal end of the occluder 29 and can optionally indwell within the patient to assist with anchoring and/or occlusion or otherwise, if desirable (see FIGS. 7A through 7D).

Figure 5A:
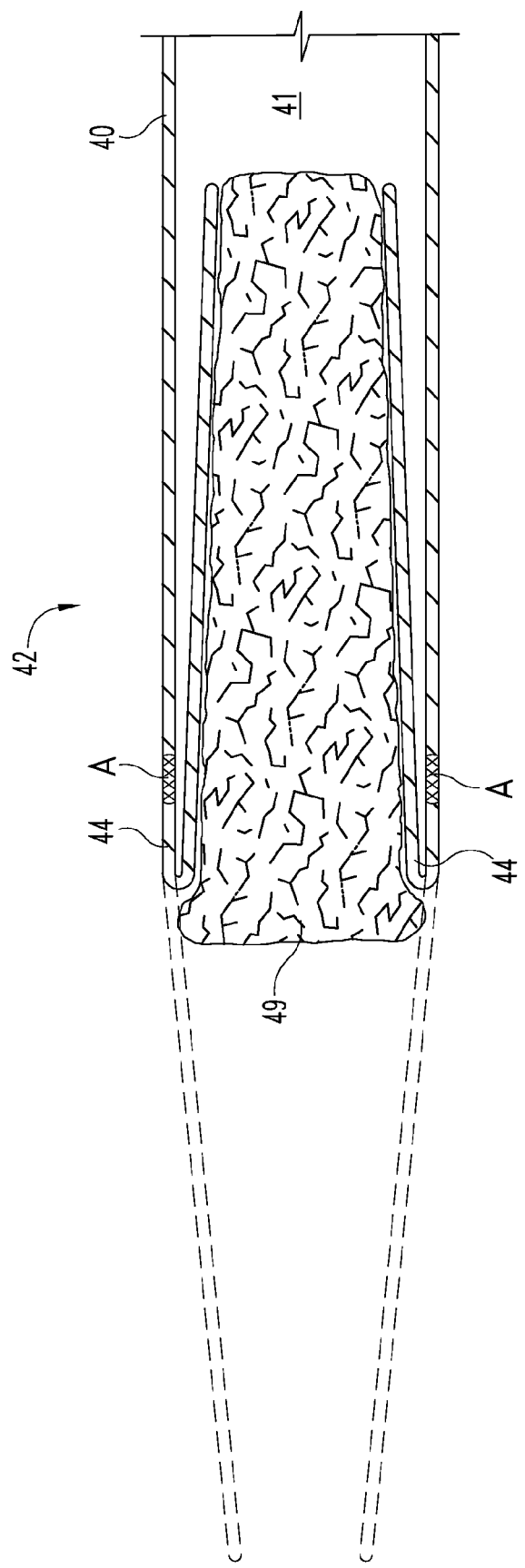
FIG. 5A depicts a cross-sectional view of an illustrative deployment device that can be useful in certain embodiments of the invention.

Turning now to FIG. 5A, an illustrative medical product 42 is depicted that can include a sheath or tube 40 having a reversible wall segment or section 44 that is configured to avert from an inverted position within the lumen 41 of the device to deploy a prosthesis 49. As shown, the wall of the sheath 40 can include a transition point or area A where the wall material transitions from a more rigid or stable wall section to a foldable or reversible wall section 44. In certain embodiments, the transition area A can include a bond, such as when the sheath is created from two or more different wall segments. Such segment bonding can be achieved with use of one or more suitable adhesives, as are within purview of one skilled in the art, or with any suitable welding technique, e.g. butt welding, or using any other suitable bonding techniques. In alternative embodiments, the transition area A can include a wall region of differing material properties, such as is exhibited by a change in flexibility of the sheath wall material. An illustrative such change in wall properties can be created by extruding the sheath 40 using an intermittent extrusion process so as to reduce the durometer of the sheath wall material within region A and throughout the reversible wall section 44. Such suitable intermittent extrusion processes can include, for example, the Total Intermittent Extrusion (T.I.E.) process by Putnam Plastics Corp. of Dayville, Conn.

With reference still to FIG. 5A, an occlusive prosthesis 49 can be located within a section of foldable wall material 44 that is reversed within the lumen 41 of the sheath 40. Illustratively, the occluder 49 can be positioned within the lumen of the sheath, by either everting or inverting the foldable wall segment 44 for example, such that a portion of the distal end of the occluder 49 extends from the sheath 40 to form a tip, e.g. an atraumatic tip. Additionally, the cross-sectional diameter and/or expansive nature of the occluder 49, in relation to the diameter of the sheath 40, can be sufficient to form a substantially fluid tight seal between the occlusion device and the reversed section of wall material 44.

Figure 5B:
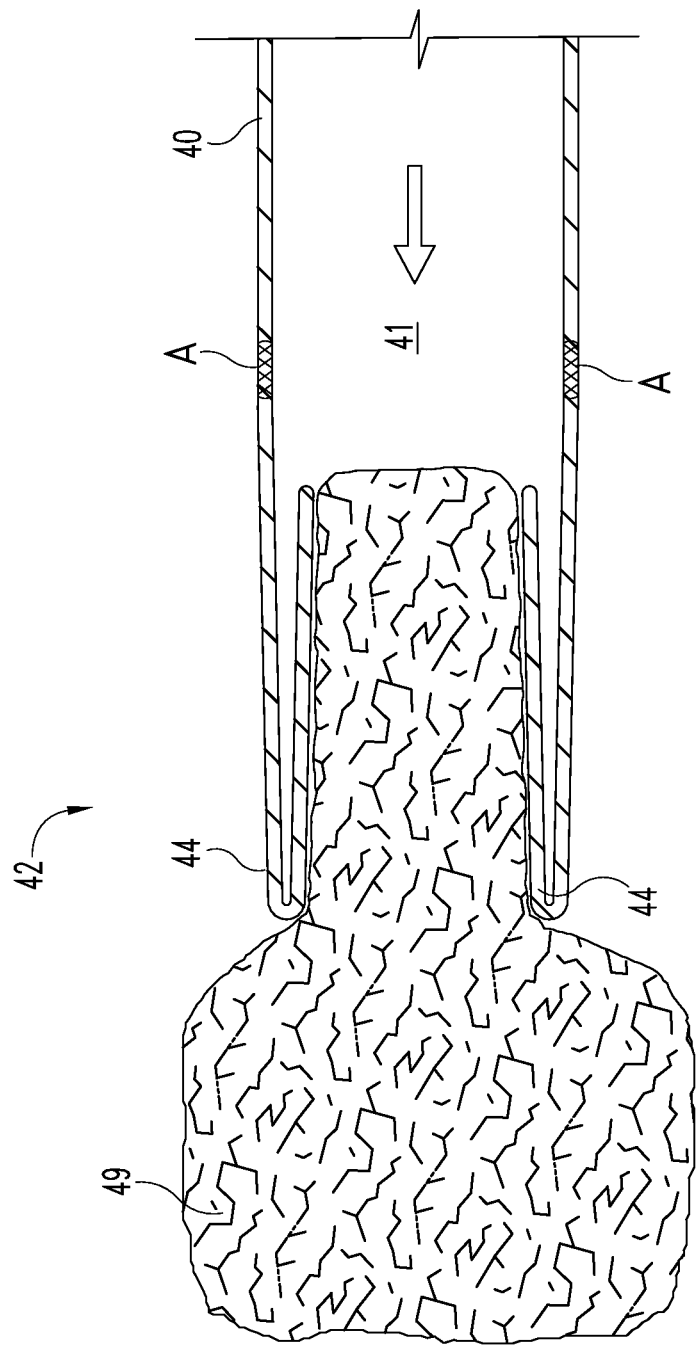
FIG. 5B depicts a cross-sectional view of an illustrative deployment device that can be useful in certain embodiments of the invention.

Turning now to FIG. 5B, in certain embodiments, the occluder 49 can be deployed within a venous vessel (not shown), such as the GSV, by pressurizing (see arrow) the lumen 41 of the sheath 40 with a suitable material, such as a liquid, e.g. saline potentially doped with a sclerosive agent for example, so as to avert the inverted wall segment and deliver the occluder 49 into the vessel. Illustratively, the diameter of the foldable wall segment 44 can exhibit a taper or bore that decreases in a distal direction from wall region A and that can serve to facilitate eversion of the folded wall segment (also see broken lines in FIG. 5A).

During certain deployment procedures, the sheath 40 can be retracted in a proximal direction while deploying the occluder 49, or alternatively, the sheath 40 can be held stationary, or moved distally, during deployment so as to vary the deployment location, as is desirable. Additionally, a pusher (not shown) or other suitable device can be used to assist with the deployment of the occluder 49, such as to assist with completing delivery, in instances where the fluid pressure is relieved just prior to the release of the occluder from the reversed wall section, for example. In yet additional embodiments, the distal end of the sheath 40 can include a distal cap or wall that extends across the face of the distal sheath end. The cap can serve to isolate a pressurization fluid from the occluder 49, and/or can serve to assist with device deployment. The closed end, as well as the occluder 49, can include an aperture for receiving a wire guide that can be used to assist with placement of the medical product 42 and/or deployment of the occluder 49 within a bodily vessel, if desirable.

Figure 6A:
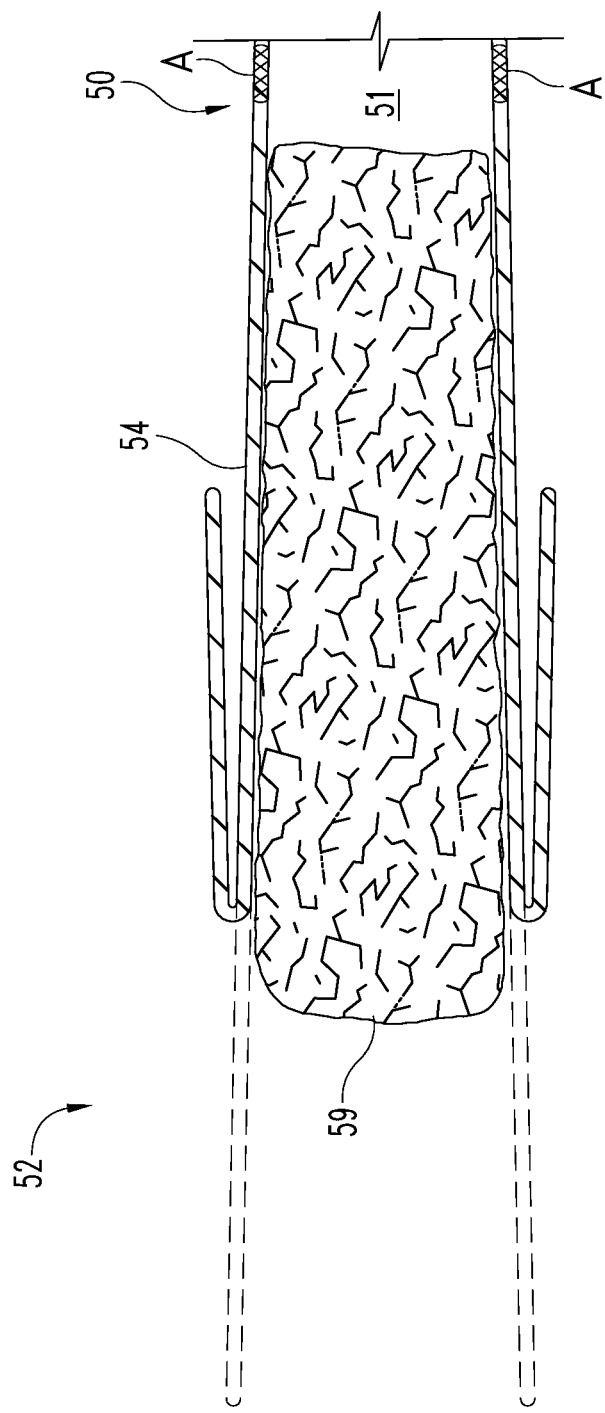
FIG. 6A depicts a cross-sectional view of an illustrative deployment device that can be useful in certain embodiments of the invention.

Turning now to FIG. 6A, an illustrative medical product 52 is depicted having a sheath 50 that includes a reversible or foldable wall segment 54, at least a portion of which contains an occlusive prosthesis 59. The wall of the sheath 50 can transition A from a more rigid material extending through the proximal sheath end to a material or material composition 54 that extends through the distal sheath end and that is flexible enough to be outwardly reversible over itself. The material properties of the sheath, e.g. durometer, can be varied to impart flexibility to the reversible wall section 54 using techniques as are discussed herein. Additionally, in certain embodiments, the material properties of the entire sheath wall can exhibit a lesser durometer, and be readily flexible, such that the entire sheath wall can be outwardly reversed over itself and is also readily compliant within a vessel, so as to be substantially self guiding, for example.

Further, as is depicted in FIG. 6A, sheath wall 54 eversion can be facilitated by a taper in the sheath wall, such as a gradual change in the overall diameter of the sheath wall and/or a change in the outer diameter of the sheath wall. In certain embodiments, the sheath 50 taper will provide for ready eversion of the sheath wall over itself and will also desirably reduce or eliminate the need for lubricants to promote wall eversion.

Turning now to a discussion of sheath 50 tapering techniques that can facilitate reversal of the sheath wall 54, in certain embodiments, the sheath taper can comprise a gradual reduction in the sheath's wall diameter from the distal tip of the sheath 50, through region A, to the proximal end of the sheath 50. In alternative embodiments, the sheath taper can include a gradual reduction in the outer sheath wall diameter from the distal end of the sheath 50 to the proximal end of the sheath. Additionally, only a portion or segment of the sheath diameter and/or outer sheath wall diameter that is necessary to provide sufficient wall reversal for the deployment of one or more prosthesis can downwardly taper in a proximal direction, such as where the distal sheath end indwells during deployment and is actuatable using one or more leaders or wires, as is discussed herein. In alternative embodiments, a suitable taper, as well as sufficient flexibility can be imparted into a sheath wall by pulling or stretching at least a portion of a suitable sheath until the sheath wall will readily ever over itself.

Figure 6B:
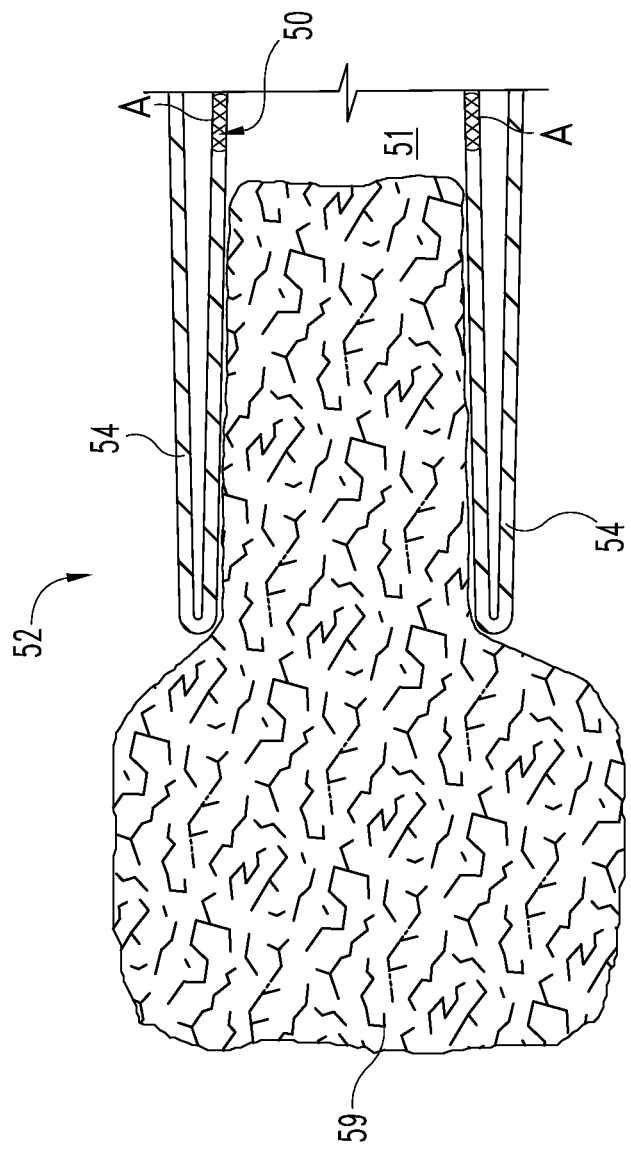
FIG. 6B depicts a cross-sectional view of an illustrative deployment device that can be useful in certain embodiments of the invention.

Turning now to FIG. 6B, the occlusion device 59 can be deployed within a vascular vessel (not shown) by moving the reversed portion of the reversible wall segment 54 in a proximal direction along the sheath wall. Illustratively, as is discussed herein, the reversed segment of reversible sheath wall 54 can be of sufficient length to extend to an extracutaneous location so as to be actuatable by a user at the extracutaneous location to deploy the occluder 59 at a vascular site. Alternatively, the reversible segment 54 can be actuated at an intracutaneous location by attaching one or more control wires, or other means to the reversible wall segment 54, as is discussed herein. The control wires can extend to an extracutaneous location where they can be actuated to deploy the prosthesis 59. In yet still another embodiment, the free end of the reversible wall segment 54 can be outwardly folded over itself and attached to a cannulated device that is annularly received over the deployment sheath 50. The cannulated device can extend along the sheath wall to an extracutaneous location where it can be actuated by a user to deploy the prosthesis. In still alternative embodiments, the reversible wall segment 54 can be actuated from an unfolded position within a patient so as to deploy the prosthesis, if desirable.

Turning now to a discussion of certain illustrative occlusion methods of the invention, with general reference to FIGS. 7A through 7D, shown is an enlarged view of that portion of the human leg occurring generally between points 13 and 14 of FIG. 1. In a certain deployment procedure, percutaneous access to the GSV 10 can be achieved at point 13 using the Seldinger or any other suitable technique. For instance, an access needle (not shown) can be passed through the skin to access the GSV 10, and a wire guide (not shown) can be passed through the access needle and into the vein 10. Prior to the deployment of an occlusion device 79, 74, the wire guide can be used for any number of conventional procedures including catheterization and imaging procedures in order to locate the sapheno-femoral junction 12. After any such preliminary procedures that are performed, the wire guide can be used to place an introducer sheath (not shown) at point 13 and the wire guide can then be removed. Thereafter, a reversible deployment device containing an occlusion device 74, 79 can be introduced into the GSV 10 and the introducer sheath withdrawn, if desirable. The reversible deployment device can then be routed through the GSV, using suitable guidance techniques, e.g. ultrasonic guidance, until the distal end of the sheath 70 or the tip 77 of the occlusion device 79 is located proximate to the sapheno-femoral junction 12 near venous location point 14.

Figure 7A:
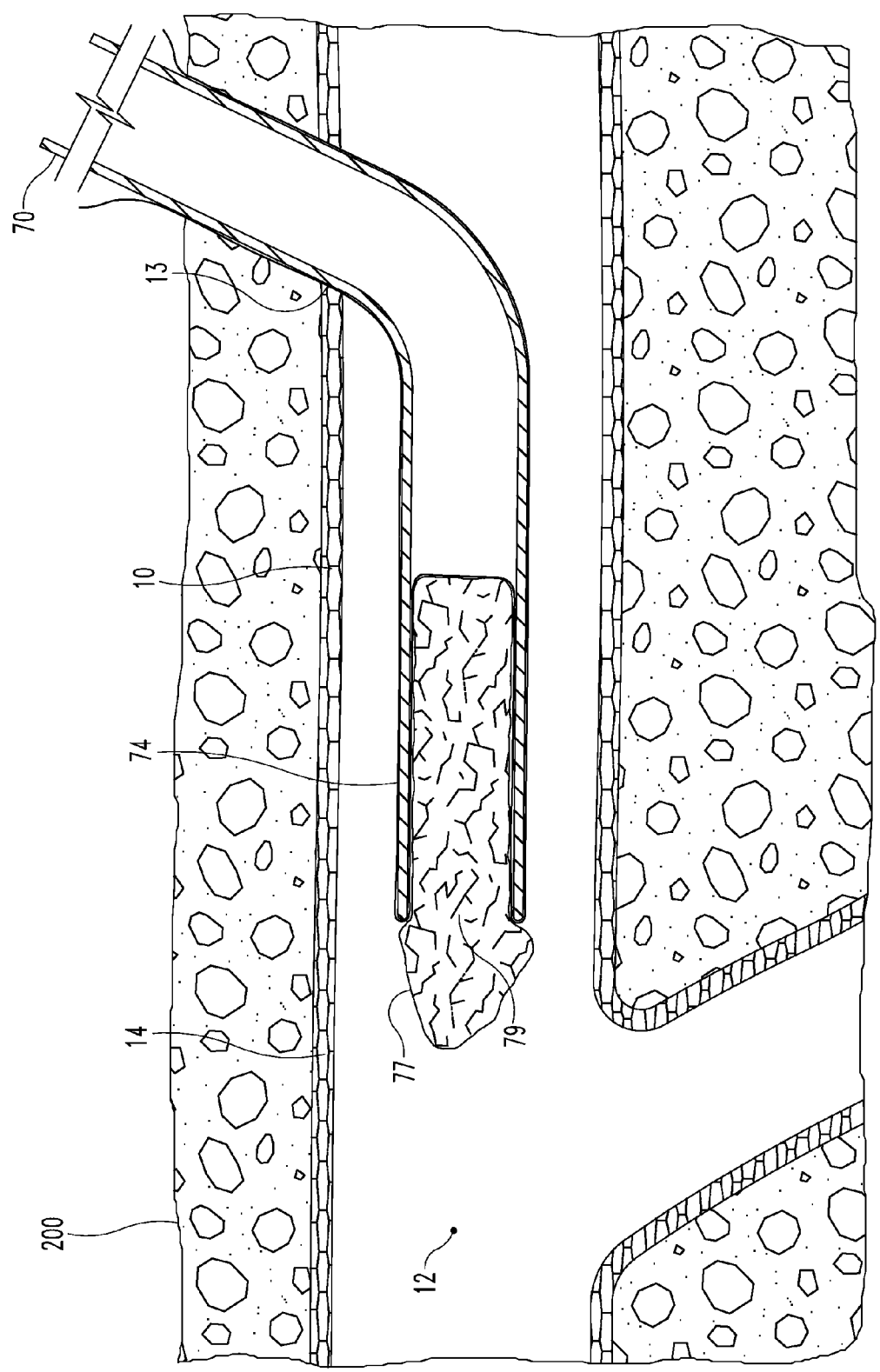
FIG. 7A depicts a cross-sectional view of an illustrative deployment procedure that can be useful in certain embodiments of the invention.

More specifically now, as is shown in FIG. 7A, the reversible deployment device can include a sheath 70 that contains an occlusive prosthesis 79 that has a distal tip 77 that can extend from the distal end of the sheath and that can be fashioned into an atraumatic bullet nosed shape so as to enhance the guidance of the deployment device through the GSV 10. The proximal end of the occlusion device 79 can be attached to a flexible sleeve 74, the sleeve optionally having a closed distal end. Illustratively, the sleeve can comprise a remodelable material, as discussed below, as well as in U.S. Pat. No. 6,358,284, that can be fashioned into a tube, and the occluder 79 can comprise a remodelable sponge form mate-rial, as is also discussed below. As shown, the sleeve 74 can encompass or wrap around the occluder 79 within the sheath 70 and can also reverse around the distal end of the sheath and extend along the sheath 70 wall to an extracutaneous, readily actuatable location.

Figure 7B:
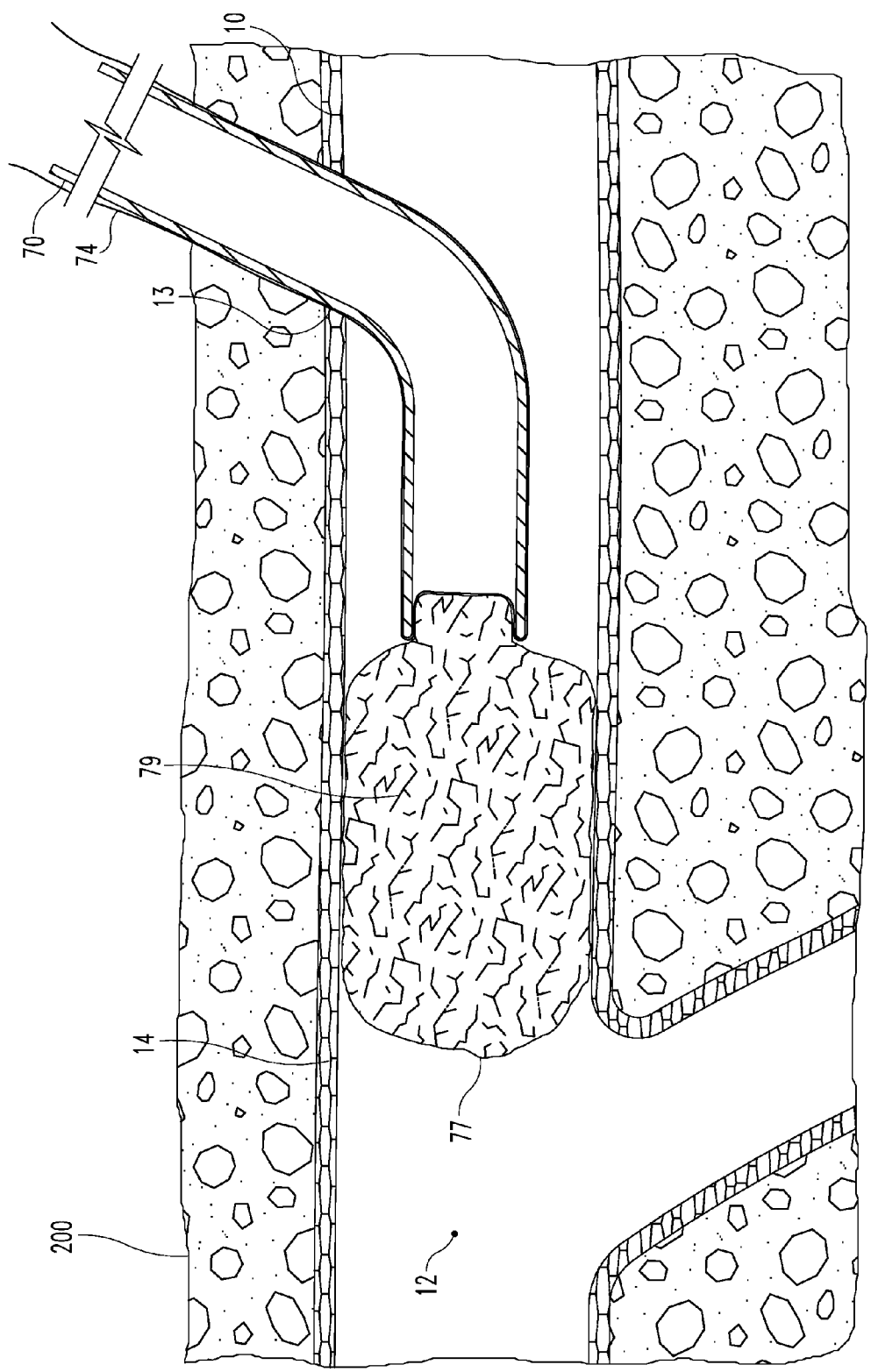
FIG. 7B depicts a cross-sectional view of an illustrative deployment procedure that can be useful in certain embodiments of the invention.

Turning now to FIG. 7B, the occluder 79 can be deployed within the GSV 10 by actuating, e.g. moving in a proximal direction, the sleeve 74. As the occluder 79 leaves the lumen of the sheath 70, it can expand within the GSV 10. Such occluder expansion can be facilitated by contact with blood or other fluids, such as those delivered through the sheath lumen, so as to achieve occlusion of the vessel 10. In certain embodiments, the occluder 79 can be deployed from the sheath 70 in successive stages, so as to provide sufficient time for the exposed portions of the occluder 79 to expand within the GSV 10 and become anchored, if desirable. This anchoring of occluder 79 segments during deployment can assist with the deployment of the occluder 79 by providing for the movement of the sheath 70 and sleeve material 74 in a proximal direction with respect to the partially anchored occluder 79.

Figure 7C:
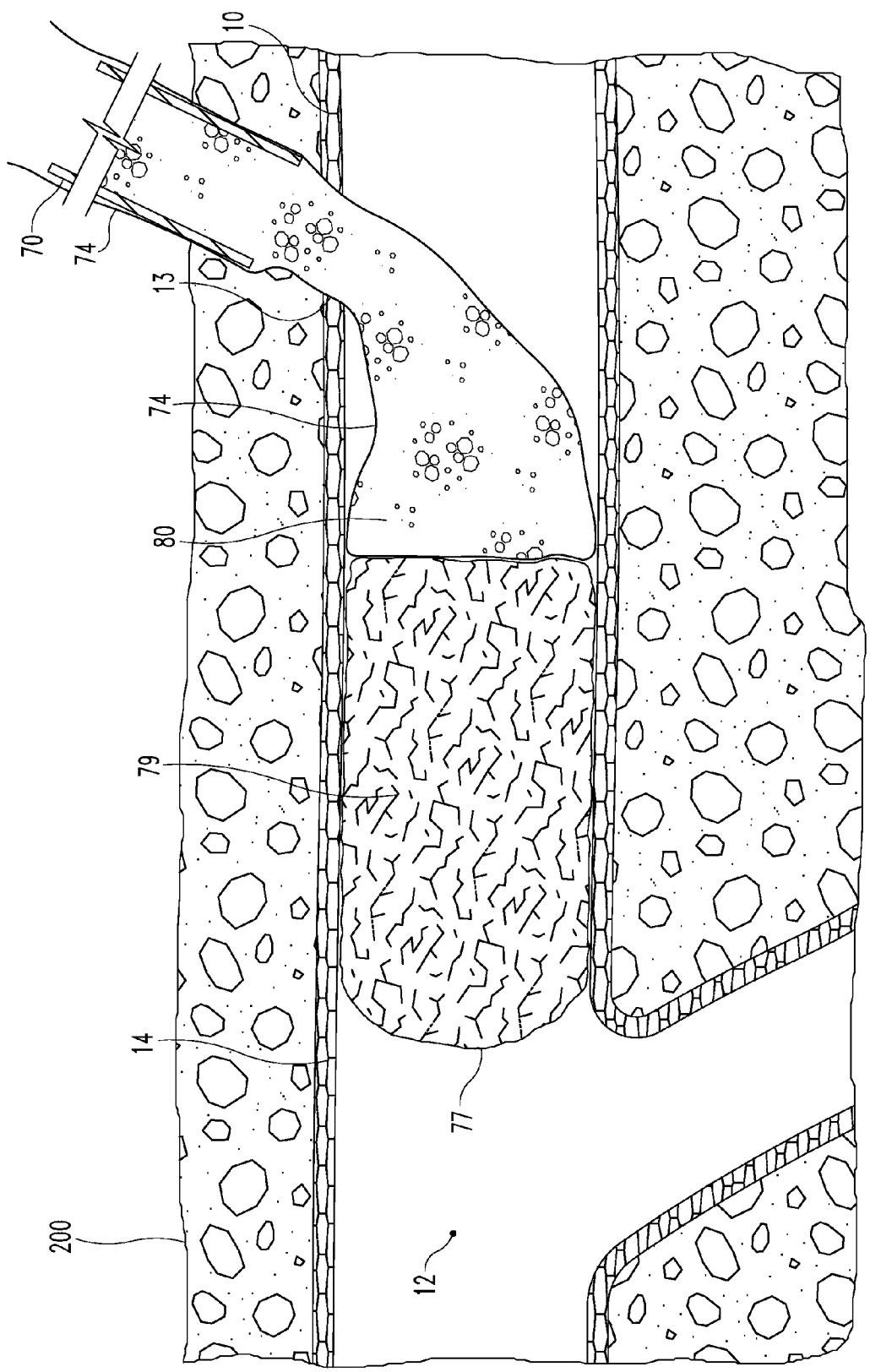
FIG. 7C depicts a cross-sectional view of an illustrative deployment procedure that can be useful in certain embodiments of the invention.

With reference now to FIG. 7C, in certain embodiments, the occluder 79 can be deployed within the vessel 10 to occupy a portion of the venous path between venous points 13 and 14. Additionally, the attached sleeve 74 can continue through any suitable segment of the remaining venous pathway, as is desirable, such as by extending along the vein from the occluder 79 and through access point 13. As is shown, a suitable fill material 80, discussed herein, e.g. a flowable remodelable material, can be used to inflate or fill the sleeve 74 so as to facilitate the closure of the passageway between venous points 13 and 14 (see FIG. 7D). Illustratively, the fill material can be passed through the lumen of the sheath 70 so as to fill and expand the sleeve 74 within the venous lumen 10 and/or enhance the closure of the occlusion device, such as by flowing into and out through portions of the occlusion device so as to fill void spaces between the vessel wall and the occlusion device.

Additionally, any other suitable material can be passed into the vessel 10 through the sleeve 74 lumen in addition or instead of fill material. For example, a suitable fluid, such as saline, can be passed through the sleeve 74, such as during occluder 79 deployment, so as to wet the occluder 79 body to enhance its expansion within the vessel 10. Additionally, a suitable therapeutic agent can be passed through the sleeve 74 lumen either during and/or after deployment of the occluder 79 within the GSV 10. Illustrative such therapeutic agents can include one or more vasoconstrictive agents, sclerosive agents, or any suitable combination thereof, whereas such agents can be effective to stimulate patient tissue to remodel a remodelable occlusive prosthesis 79 and/or sleeve 74 and/or otherwise facilitate vessel 10 closure.

Figure 7D:
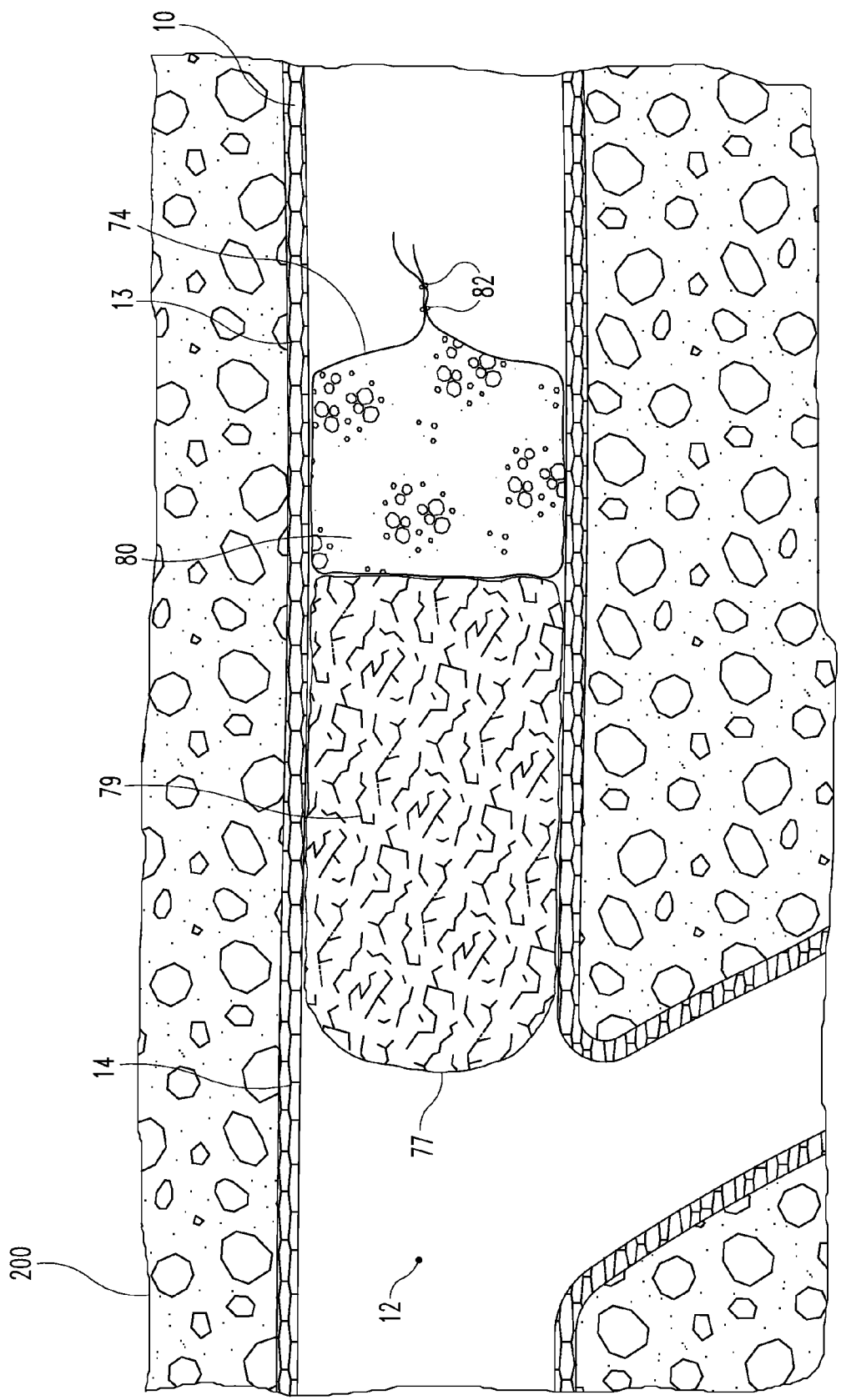
FIG. 7D depicts a cross-sectional view of an illustrative deployment procedure that can be useful in certain embodiments of the invention.

With reference now to FIG. 7D, as is shown, the occlusive prosthesis 79, in combination with a filled remodelable sleeve 74 can serve to substantially occlude the venous passageway extending between points 13 and 14 in the GSV 10 so as to treat certain varicosities resultant of VVI. As depicted, the proximal end of the inflated reversible sleeve 74 can be sealed by placing one or more elastic cuffs 82 over the sleeve material 74. Illustratively, cuff placement can be facilitated by locating the cuffs within the GSV 10 over the sheath and sleeve while the sheath is still disposed within the lumen of the sleeve and the distal end of the sheath is still located within the GSV 10, proximate to venous point 13 for example. In alternative embodiments, the proximal end of the sleeve 74 can extend through the GSV 10 wall and can be tied to patient tissue, such as with one or more sutures or staples, so as to seal the sleeve lumen and/or serve to enhance anchoring of the occluder within the GSV 10. For more information concerning methods and devices for anchoring and sealing occlusion devices that can be useful in certain embodiments of the invention, reference can be made, for example, to U.S. patent application Ser. No. 10/999,173, entitled "Vascular Occlusion Methods, Systems, and Devices," filed on Nov. 29, 2004 and/or U.S. Provisional Patent App. Ser. No. 60/640,544, entitled "Inverting Occlusion Devices, Methods, and Systems," filed on Dec. 30, 2004 and/or U.S. Provisional Patent App. Ser. No. 60/633,543, entitled "Inflatable Occlusion Devices, Methods, and Systems," filed on Dec. 6, 2004.

Turning now to a discussion of illustrative loading methods of the invention, in certain aspects, a sheath having a reversible segment can be used to load or otherwise swallow or envelope a suitable deployable device, such as a deployable device having low radial force or a device not able to withstand longitudinal forces needed to push the device into a deployment sheath. For example, the reversible component can be reversed, folded, or located so as to provide a fold in the reversible component at the location that will contact the proximal end of the loaded deployable device. Thereafter, the proximal end of the deployable device can be contacted to the reversed component and the reversed component can be actuated in a fashion so as to cover, envelope, swallow, or otherwise enclose at least a portion of the deployable device within the lumen of the sheath.

Illustratively, any suitable device can be deployed within any suitable portion or segment of the vasculature or other bodily lumen using a reversible sheath of the invention. Some such advantageously deployable devices can include devices that have low radial force and/or devices that tend to buckle, compress, or twist under longitudinal forces caused by current deployment and/or device loading techniques. Such deployable devices can include self-expandable or non-self expandable stents, grafts, stent-grafts, filters, valves, occluders, and/or the like. Additionally, such stents can include stents for excluding aneurysm, dilating vessels, and or stents that can serve as vascular valves, such as those that incorporate remodelable leaflet material. For more information concerning prosthetic stent valves that can be useful in certain aspects of the present invention, reference can be made, for example, to U.S. Pat./App. Nos. 2001/0039450, 2004/0186558, U.S. Pat. Nos. 6,126,686, 6,589,279, and/or International Publication No. WO2004/082528, dated Sep. 30, 2004, publishing International Application No. PCT/IS2004/008176, filed Mar. 17, 2004 and/or International Publication No. WO2004/089253, dated Oct. 21, 2004, publishing International Application No. PCT/IS2004/009971, filed Apr. 1, 2004, and/or U.S. Utility application entitled "Implantable Frame with Variable Compliance," filed on Apr. 11, 2005, and claiming priority to U.S. Provisional Application Ser. No. 60/561,739 entitled "Implantable Frame with Variable Compliance," filed on Apr. 13, 2004.

Turning now to a discussion of sheath materials that can be useful in forming reversible sheaths of the invention, such reversible sheaths can be formed using any suitable biocompatible material, such that at least a portion of the sheath wall can be folded or reversed over itself so as to deploy a prosthesis. Illustrative such sheath materials can include any suitable materials, such as polyurethane, Pebax®, polyethylene, polyethylene terephthalate (PET), PTFE (e.g. Teflon), or polyamide (e.g. Nylon) material, or a combination of such materials, such as by bonding a reversible sheath section to a non-reversible sheath section where the non-reversible section can include an inner layer of PTFE, a flat wire coil over the PTFE for kink resistance, and a polyamide (Nylon) outer layer to provide integrity to the overall structure and a smooth surface (e.g. as in the Flexor sheath, Cook Incorporated), for example. In certain embodiments, a reversible wall segment or component can be formed by pulling or otherwise stretching a sheath, such as a PET sheath, or a suitable portion thereof, until the wall portion will readily reverse over itself, and then optionally tapering either the sheath diameter or the outer wall diameter of the sheath, if necessary (such as when the taper is not sufficiently imparted to the sheath during stretching), to facilitate wall reversal along the appropriate length of the sheath, as is discussed above. Alternatively, a reversible wall segment or component can be formed by extruding a sheath, comprising Pebax® or polyurethane for example, using a suitable intermittent extrusion process that can vary the durometer of portions of the sheath as is desirable, as is discussed above.

Illustrative rigid or semi-rigid sheaths useful in certain aspects of the invention, such as reversible sleeve embodiments, can comprise any standard sheath as is known in the art. Illustrative such sheaths can be directionally tapered, if desirable, using hot or cold forming techniques and/or lathe type milling or machining techniques. Illustrative such sheath materials can include any of those mentioned above and/or any materials that are within the purview of one of ordinary skill in the art.

Illustrative sleeve materials that can be useful in certain embodiments of the invention, can include any suitable flexible biocompatible material. Such suitable biocompatible materials can include, for example, polyamide, silicone, latex, PTFE, and/or any suitable remodelable material, as are discussed herein. Such materials can be fashioned into a tubular form, for example, using any suitable technique as is known in the art and can be attached to the occlusive prosthesis, as is desirable, using any technique, such as one or more suitable bonding techniques and/or agents, sutures, and/or staples or the like. Illustratively, when the sleeve and the occlusion device each comprise an extracellular matrix (ECM) material, such suitable bonding techniques can include dehydrothermal bonding techniques, under evaporative cooling conditions, if desirable. For more information concerning ECM material bonding that can be useful in certain embodiments of the present invention, reference can be made, for example, to U.S. Pat. No. 6,358,284.

Turning now to a discussion of materials that can be used to form medical devices that can be useful in certain embodiments of the present invention, e.g. stent frames and/or occlusion anchoring devices, such as barbs, suitable such materials can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof. Illustrative resorbable synthetic materials can include polylactic acid, polyglycolic acid or copolymers thereof, a polyanhydride, polycaprolactone, polyhydroxybutyrate valerate, polyhydroxyalkanoate, or another biodegradable polymer or mixture thereof. Illustrative metals and metal alloys can include nitinol or other shape-memory materials, or stainless steel. For further information concerning suitable materials (biodegradable, nonbiodegradable, and metallic), useful in certain embodiments of the present invention, reference can be made, for example, to U.S. Utility patent application titled, "Implantable Frame with Variable Compliance," filed on Apr. 11, 2005 ("Express Mail" Mailing Label No. EV 327 135 804 US), which claims priority to U.S.

Provisional Patent Application Ser. No. 60/561,739 entitled, "Implantable Frame with Variable Compliance," filed on Apr. 13, 2004.

Turning now to a discussion of materials that can be used to form occlusion devices, valve leaflets, and/or stent covering material that can be useful in certain embodiments of the present invention, such materials can include any suitable biocompatible material. Generally, such materials may include a remodelable material, such as a resorbable synthetic material, e.g. polyvinyl alcohol foam, or a naturally derived resorbable or remodelable material. Additionally, such materials can include any other suitable naturally derived or any other suitable nonresorbable synthetic material, or any combination of any of the above such biocompatible materials. Such biocompatible materials that are at least bioresorbable will provide advantage in certain embodiments of the invention, with materials that are bioremodelable or otherwise tissue inductive so as to promote cellular invasion and ingrowth providing particular advantage. Illustratively, remodelable materials may be used in this context to provide an occlusive prosthesis that promotes cellular growth within the prosthesis to promote occlusion or closure of a bodily lumen that is sealed by the prosthesis.

Suitable remodelable materials can include collagenous extracellular matrix (ECM) materials, such as submucosa, renal capsule membrane, dura mater, pericardium, serosa, peritoneum, or basement membrane. Preferred remodelable material will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in certain embodiments of the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in aspects of the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

As prepared and used, the submucosa material or any other ECM material may optionally retain growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in certain embodiments of the invention may retain other biological materials such as heparin, heparin sulfate, hyaluronic acid, fibronectin and the like. Thus, generally speaking, the submucosa or other ECM material may retain a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances or therapeutic agents. Illustrative drug substances that may be incorporated into and/or onto the ECM material can include, for example, antibiotics and/or thrombus-promoting substances such as blood clotting factors, e.g. thrombin, fibrinogen, and the like. Illustrative therapeutic agents that may be incorporated into and/or onto the ECM material can include, for example, vasoconstrictors, sclerosants, or any suitable combination thereof. These substances may be applied to the ECM material as a premanufactured step, immediately prior to application (e.g. by soaking the material in a solution containing a suitable antibiotic such as cefazolin), or during or after application of the ECM material to the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material useful in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa useful in certain embodiments of the present invention.

Turning now to a discussion of foam or sponge form materials that can be incorporated into occlusive prosthesis that can be useful in certain embodiments of the present invention, such foam or sponge form materials can include any suitable biocompatible sponge or foam material. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers, e.g. polyvinyl alcohol foam. More preferred sponge compositions will comprise collagen as a matrix-forming material, either alone or in combination with one or more other matrix forming material. In general, sponge matrices useful in certain embodiments of the invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collageneous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. Preferably, the crosslinking agent will contain polar groups that impart a hydrophilic character to the final sponge matrix material. Desirably, a polyepoxide crosslinker is utilized for this purpose, especially a polyglycidyl ether compound. Suitable such compounds can include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized will have from 2 to about 10 epoxide groups per molecule. The use of such epoxides and/or other crosslinking agents which impart polar groups and a hydrophilic character to the resulting matrix will provide for good wettability and rapid hydration and expansion of occlusive devices of the invention.

Preferred sources of collagen for forming sponge matrices useful in certain embodiments of the invention include extracellular matrix materials such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials that can be used to form illustrative devices of the invention can be highly expandable when wetted, so as to achieve an expanded configuration. Illustratively, expandable sponge materials can exhibit the capacity to expand at least 100% by volume, or at least about 200% by volume, and in certain aspects in the range of about 300% by volume to about 1000% by volume, when wetted to saturation with deionized water. Sponge materials useful in embodiments of the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming occlusive bodies that can be useful in embodiments of the invention can be highly dense, typically having densities of at least about 0.05 $g/cm^3$, preferably in the range of about 0.05 $g/cm^3$ to about 0.2 $g/cm^3$, and more preferably about 0.075 $g/cm^3$ to about 0.2 $g/cm^3$. Expanded sponge densities (dry) will generally be less than the corresponding compacted densities. Typical expanded densities (dry) will range from about 0.01 $g/cm^3$ to about 0.1 $g/cm^3$, more preferably about 0.02 $g/cm^3$ to about 0.07 $g/cm^3$.

Compressed sponge materials may also contain agents which promote further retention of the compressed, high density form of the matrices. These may include for example starch, cellulose, sugars such as dextrose, or glycerin. Additionally, sponge materials may also contain one or more therapeutic agents, such as vasoconstrictors, sclerosants, or any suitable combination thereof. Such agents can optionally be included in the liquid (preferably aqueous) used to hydrate or otherwise wet the sponge prior to compaction and drying. For additional information concerning foam or sponge form materials that can be useful in certain embodiments of the present invention, reference can be made, for example, to U.S. Pat. App. Pub. No. 2003/0013989.

The remodelable ECM or other material may include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within the ECM or other remodelable material, such that, for example, the location of the balloon's distal end is detectable.

Turning now to a discussion of fill materials that can be used to facilitate occlusion of a bodily lumen, such as by filling the lumen of an implanted sleeve segment (see FIGS. 7A-7D for example) or by being injected within the lumen and/or an occlusive device to fill voids or otherwise enhance closure, suitable fill materials can include any material conducive to facilitating chronic occlusion of a bodily vessel of interest. In this regard, the fill material may be a solid, liquid, gel, foam or gas, such as blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof.

Additionally, the fill material can comprise a comminuted, fluidized, flowable, and/or gelatinous remodelable material, optionally containing a sclerosant, if desirable. For example, suitable flowable, remodelable ECM materials can be prepared, for example, as described in U.S. Pat. Nos. 5,275,826, 5,516,533, 6,206,931, or in International Publication No. WO2005020847 (Cook Biotech Incorporated) published Mar. 10, 2005, which are each hereby incorporated by reference in their entirety. Such flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth. This flowable remodelable composition can be used as fill material in certain aspects of the invention.

Alternatively, the fill material can comprise a suitable solidifying polymer, such as HEMA. Upon addition of a catalyst to HEMA at a certain temperature, HEMA will gradually change from a liquid form to either a gelatinous or solid form over approximately twenty minutes. This change in form is desirable in a fill material because the material can easily flow into an area to be occluded, thereby eliminating undesirable void space, and then solidify, thereby enhancing occlusion of the cavity. For more information on HEMA and other fill materials that can be useful in certain embodiments of the present invention, reference can be made, for example, to U.S. Pat. Nos. 4,819,637, 5,222,970, 5,304,123, 5,411,475, 5,830,228, and/or U.S. Provisional Patent Application Ser. No. 60/633,543 entitled "Inflatable Occlusion Devices, Methods, and Systems," filed Dec. 6, 2004, and/or U.S. Provisional Patent App. Ser. No. 60/640,544 entitled "Inverting Occlusion Devices, Methods, and Systems," filed on Dec. 30, 2004.

Additionally, in certain embodiments, the fill material, including, e.g. remodelable ECM fill materials, can include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

Turning now to a discussion of therapeutic agents that can be useful in certain embodiments of the invention, illustratively, suitable therapeutic agents can include any agent capable of bringing about a constriction, spasm or healing response in patient tissue, such as a wall segment of a venous vessel. Illustratively, such therapeutic agents can be delivered into the vessel to be occluded either before, during, or after deployment of the occlusion device, such as by being delivered through the lumen of an implanted delivery sleeve, as is discussed herein. Illustrative such therapeutic agents can include any suitable vasoconstrictive agent, sclerosive agent, or any suitable combination of one or more of any of the above agents. For example, suitable vasoconstrictive agents can include, any suitable alpha adrenergic direct or indirect agonist, such as norepinephrine, epinephrine, phenylephrine, and/or cocaine, or lidocaine, hypertonic saline, or any suitable combination thereof. Illustrative sclerosive agents can include, for example, sodium tetradecyl sulfate, morrhuate sodium, ethanolamine oleate, tetradecyl sulfate, tetracycline, glycerin, hypertonic glucose, talc, acetic acid, alcohol, bleomycin, picibanil, ethibloc, deoxycycline, and/or any suitable microfoam that contains a sclerosive agent, such as VARISOVE®, manufactured by Provensis, Ltd. of London, England, or an agent as disclosed in U.S. Pat. Nos. 5,676,962 and/or 6,572,873, for example, and/or any suitable combination thereof. Additionally, therapeutic agents can comprise any suitable combination of any of the above listed vasoconstrictive and/or sclerosive agents.

Occlusion devices that can be useful in certain embodiments of the invention can include any such device or graft construct that is suitable for occluding a bodily lumen of a patient. Illustrative such occlusive prosthetics can include many ECM or other graft constructs. For example, in certain embodiments, an occlusive prosthesis can include an ECM sheet material, folded in half, fan folded, folded in half after being fan folded, or otherwise, for example. Additionally, suitable ECM occlusive graft constructs can include rolled sheet material that can be optionally compressed and lyophilized for example and that can contain one or more surface protuberances and/or cuts and that can include one or more anchors, such as a self expandable stent, at each end of the device or otherwise. Alternatively, suitable occlusive constructs can comprise coils, such as ECM embolic coils or the like, and or any combination of the above. For more information on occlusive graft products that can be useful in certain embodiments of the invention, reference can be made, for example, to U.S. Utility application Ser. No. 10/999,173, entitled "Vascular Occlusion Methods, Systems and Devices," filed Nov. 29, 2004.

Occlusion devices that can be useful in certain embodiments of the invention will generally be of sufficient dimension to achieve occlusion of the desired stretch of vascular vessel, either alone or in combination with other similar or differing devices. In certain embodiments, the occlusion device will have a length of at least about 10 cm, and in many situations at least about 20 cm. Indeed, for preferred occlusion procedures involving a significant stretch of an artery or vein, occlusion devices having lengths greater than 30 cm will be used. Illustratively, in the occlusion of the GSV in human adolescents or adults, occlusion devices having lengths of at least about 40 cm or 50 cm can be used.

Illustratively, delivery sheaths used in the invention for the delivery of occlusive material will have a lumen diameter sized to allow for the introduction of a sufficient amount of occlusion material to occlude the artery or vein of interest. For example, the inner diameter (I.D.) of the final delivery sheath can range from about 4 French up to about 40 French.

While discussions above focus upon occluding the GSV via access at the knee level, the GSV may also be accessed at a lower level, e.g. near the ankle. During such access, any or all of the GSV occurring between the ankle and the saphenofemoral junction may be subjected to occlusion. Other veins in the leg(s) that may be involved in the varicose vein condition may also be occluded, alternatively or in addition to the GSV. For example, the lesser saphenous vein 5 (FIGS. 1 through 3), or varicose veins themselves, may be occluded and obliterated in accordance with certain embodiments of the invention. Further, other bodily lumens, veins, or arteries, either in the leg(s) or elsewhere in the body, may be occluded or have other devices implanted in them according to embodiments of the present invention, such as by obtaining access at any suitable location, e.g. the jugular vein.

Percutaneously conducted occlusion procedures of the invention can be performed under local anesthesia, if desirable. In addition, after completion of the procedure, it may be beneficial to use graduated compression stockings in the occluded area, for example for a week or more. Compression of the occluded area may serve to facilitate permanent closure of the occluded vessel, for example when applied during a remodeling period during which tissue ingrowth into the occluded lumen occurs.

Dilators, wire guides and needles used in the present invention can all be conventional marketed products or modifications thereof. Dilators can be made from conventional dilator/catheter type materials such as polyethylene, polyamide, polyurethane or vinyl, or any combination of these materials. Fittings provided for sheath/dilator assemblies can be conventional elements such as luer locks, and the dilator can have a fitting allowing it to be locked to the sheath during insertion and manipulation.

As is conventional, the distal ends of the catheters, sheaths, dilators, wires, occlusion devices or other components used in percutaneous procedures can include markers that can be X-ray, sonographically, or otherwise non-invasively visualized to identify their location during the procedure. Metallic bands of stainless steel, tantalum, platinum, gold, or other suitable materials, which include a dimple pattern, can serve to purpose for both ultrasound and X-ray identification.

Certain embodiments of the invention can also include medical kits, such as an inventive sheath that has a reversible component that contains one or more deployable prostheses sealed within sterile medical packaging. The final, packaged product is provided in a sterile condition. This may be achieved, for example, by gamma, e-beam or other irradiation techniques, ethylene oxide gas, or any other suitable sterilization technique, and the materials and other properties of the medical packaging will be selected accordingly. The prosthesis device may be packaged wet or after it is dried.

All publications cited herein are hereby incorporated by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical product for the delivery of a prosthesis within the vasculature of a patient, comprising:
    a sponge form prosthesis, said sponge form prosthesis having a proximal end and a distal end, wherein said sponge form prosthesis is movable between a constrained position and an expanded position; and
    a cannulated device, said cannulated device having a proximal end, a distal end, a lumen, and a reversible segment, wherein the reversible segment contains the sponge form prosthesis and is reversible by a user so as to deploy the sponge form prosthesis within the vasculature of a patient;
    wherein said sponge form prosthesis is expansible at least 100% by volume when wetted to saturation with deionized water.

2. The medical product of claim 1, wherein said reversible segment comprises a sleeve, said sleeve having a proximal end, a distal end, and a lumen, wherein said sleeve lumen is disposed within said lumen of said cannulated device and said distal end of said sleeve is reversed over said distal end of said cannulated device.

3. The medical product of claim 2, wherein said sleeve comprises a synthetic material.

4. The medical product of claim 2, wherein said sleeve comprises a remodelable extracellular matrix material.

5. The medical product of claim 2, wherein said distal end of said sleeve is attached to said proximal end of said sponge form prosthesis.

6. The medical product of claim 2, wherein said distal end of said sleeve is reversed over said distal end of said cannulated device so as to position a length of said sleeve over an outermost surface of said cannulated device.

7. The medical product of claim 2, also comprising one or more actuator members connected to said sleeve at a location positioned to occur intracutaneous to a patient during use of the medical product, the one or more actuators having a length sufficient and being positioned to extend from said location to a position extracutaneous of a patient during use of the medical product.

8. The medical product of claim 1, wherein said sponge form prosthesis comprises a remodelable material.

9. The medical product of claim 1, wherein said sponge form prosthesis comprises an extracellular matrix material.

10. The medical product of claim 9, wherein said extracellular matrix material comprises submucosa.

11. The medical product of claim 1, wherein said sponge form prosthesis has a length of 0.5 cm to 60 cm.

12. The medical product of claim 11, wherein said sponge form prosthesis has a length of at least 20 cm.

13. The medical product of claim 1, wherein said reversible segment comprises an evertable distal wall segment of the cannulated device.

14. The medical product of claim 13, wherein said cannulated device has a wall, said wall having a diameter that extends between said proximal end and said distal end of said cannulated device.

15. The medical product of claim 14, wherein said wall diameter continually increases from a narrower proximal end of said cannulated device to a wider distal end of said cannulated device.

16. The medical product of claim 1, wherein said reversible segment comprises an invertible distal wall segment of said cannulated device.

17. The medical product of claim 16, wherein the invertible wall segment has a wall diameter, the wall diameter continually decreasing in a distal direction throughout the invertible wall segment.

18. The medical product of claim 1, wherein said sponge form prosthesis is porous.

19. An endoluminal medical product, comprising:
    a percutaneous deployment sheath having a proximal end, a distal end, and a wall that defines a lumen;

a sleeve having a proximal end, a distal end, and a lumen, wherein said sleeve is slidably received within said sheath lumen and said sleeve distal end extends from and reverses over said sheath distal end and wherein said sleeve is configured to deploy at least one bioremodelable prosthesis from a constrained position within said sleeve lumen to an expanded position within a patient's vasculature by reversing said sleeve around said distal end of said sheath;

wherein said bioremodelable prosthesis is configured to radially expand from said constrained position to said expanded position sufficiently to contact outer surfaces of the bioremodelable prosthesis with a wall of the patient's vasculature; wherein the bioremodelable prosthesis comprises an occlusion device;

wherein the occlusion device comprises a sponge form material; and wherein the sponge form material is expansible at least 100% by volume when wetted to saturation with deionized water.

20. The medical product of claim 19, wherein the percutaneous deployment sheath comprises PTFE or polyamide.

21. The medical product of claim 19, wherein the wall of the sheath has an outer diameter, the outer wall diameter extending between the proximal sheath end and the distal sheath end.

22. The medical product of claim 21, wherein the outer diameter increases in a proximal direction from the distal sheath end.

23. The medical product of claim 19, wherein the sleeve comprises a fabric.

24. The medical product of claim 19, wherein said sleeve distal end extends from and reverses over said sheath distal end so as to position a length of said sleeve over an outermost surface of said sheath.

* * * * *